United States Patent [19]
Batdorf et al.

[11] Patent Number: 5,549,579
[45] Date of Patent: Aug. 27, 1996

[54] UNITARY DRAIN AND METHOD FOR MAKING

[75] Inventors: David B. Batdorf, Paso Robles; Charles A. Schryver, Atascadero, both of Calif.

[73] Assignee: Specialty Silicone Fabricators, Paso Robles, Calif.

[21] Appl. No.: 506,607

[22] Filed: Jul. 25, 1995

Related U.S. Application Data

[63] Continuation of Ser. No. 219,410, Mar. 29, 1994, abandoned, which is a continuation of Ser. No. 979,808, Nov. 20, 1992, abandoned.

[51] Int. Cl.$^6$ .................................................. A61M 27/00
[52] U.S. Cl. ........................................................ 604/264
[58] Field of Search ............................... 604/93, 280, 282, 604/264, 322, 326, 284

[56] References Cited

U.S. PATENT DOCUMENTS

| | | | |
|---|---|---|---|
| 1,626,839 | 5/1927 | Kallmeyer | 604/280 |
| 3,384,089 | 5/1968 | Shriner | 604/280 |
| 3,957,054 | 5/1976 | McFarlane | 604/282 |
| 4,257,422 | 3/1981 | Duncan | 604/282 |
| 4,317,452 | 3/1982 | Russo et al. | 604/282 |
| 4,398,910 | 8/1983 | Blake et al. | 604/93 |
| 4,579,555 | 4/1986 | Russo | 604/282 |
| 5,045,075 | 9/1991 | Ersek | 604/264 |
| 5,100,395 | 3/1992 | Rosenberg | 604/284 |
| 5,141,499 | 8/1992 | Zappacosta | 604/280 |

FOREIGN PATENT DOCUMENTS

| | | | |
|---|---|---|---|
| 0414177 | 8/1910 | France | 604/264 |
| 0067140 | 12/1982 | Sweden | 604/264 |
| 0484679 | 3/1970 | Switzerland | 604/264 |
| 1204216 | 1/1986 | U.S.S.R. | 604/280 |
| 1468541 | 3/1989 | U.S.S.R. | 604/280 |
| 0006415 | 5/1886 | United Kingdom | 604/264 |

OTHER PUBLICATIONS

American Cutoscope Mailers Incorporated, Angulated soft Rubber suprapubic Drains, pp. 19 and 37.

*Primary Examiner*—Manuel Mendez
*Attorney, Agent, or Firm*—Michael G. Petit

[57] ABSTRACT

A unitary tube useful for the conduction of fluids to and from a site within the body of a patient. A particularly preferred embodiment is a drainage tube. The drainage tube, which may be continuously extruded from a biocompatible elastomer, has a variable exterior and interior cross section along its length. The drainage tube has collecting, transition and extension portions. The collecting portion, which has a hollow interior to receive fluids, is temporarily implanted within a wound site or other body cavity to enable body fluids to collect therein. The collecting portion is preferably a flattened tubular member having a width that exceeds the height. The interior wall of the collecting portion has longitudinal ribs or struts to prevent opposing walls from collapsing upon each other. The collecting portion preferably has fenestrations in its wall to permit the passage of body fluids from the surrounding tissue into the hollow interior lumen of the collection portion. The outer wall of the collecting portion tapers down by means of a transition portion to a tubular extension portion. The extension portion has a proximal end and a distal end which extends from the patient. The tube is also useful for delivering exogenous fluids to a site within the body of a patient.

1 Claim, 2 Drawing Sheets

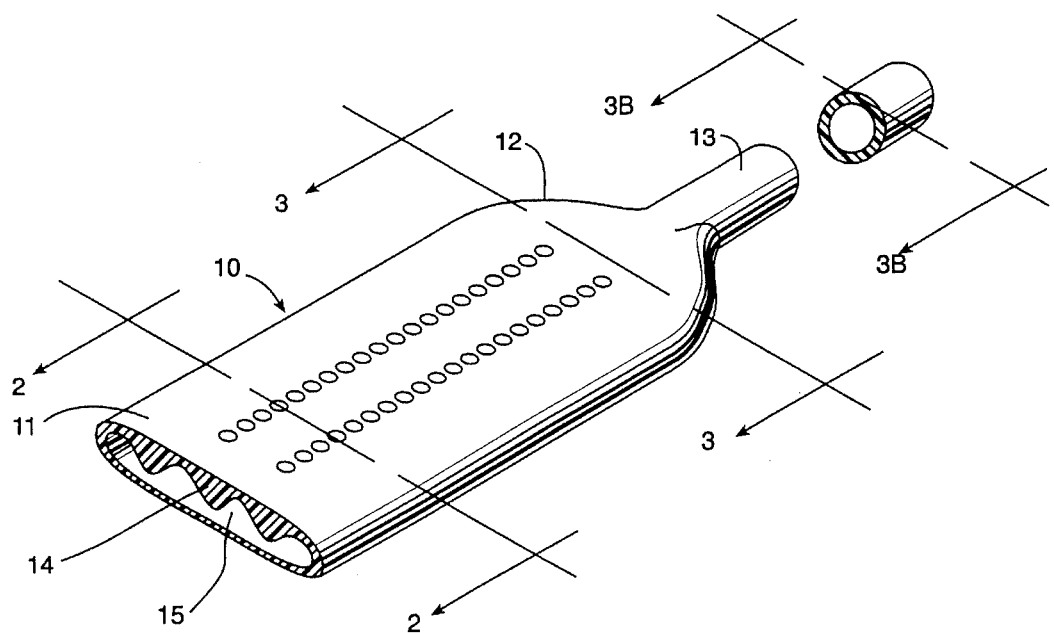
*Figure 1*
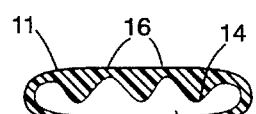
*Figure 2*
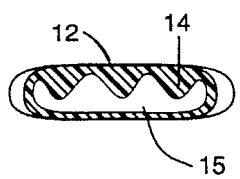
*Figure 3*
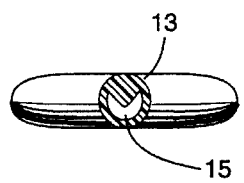
*Figure 3B*
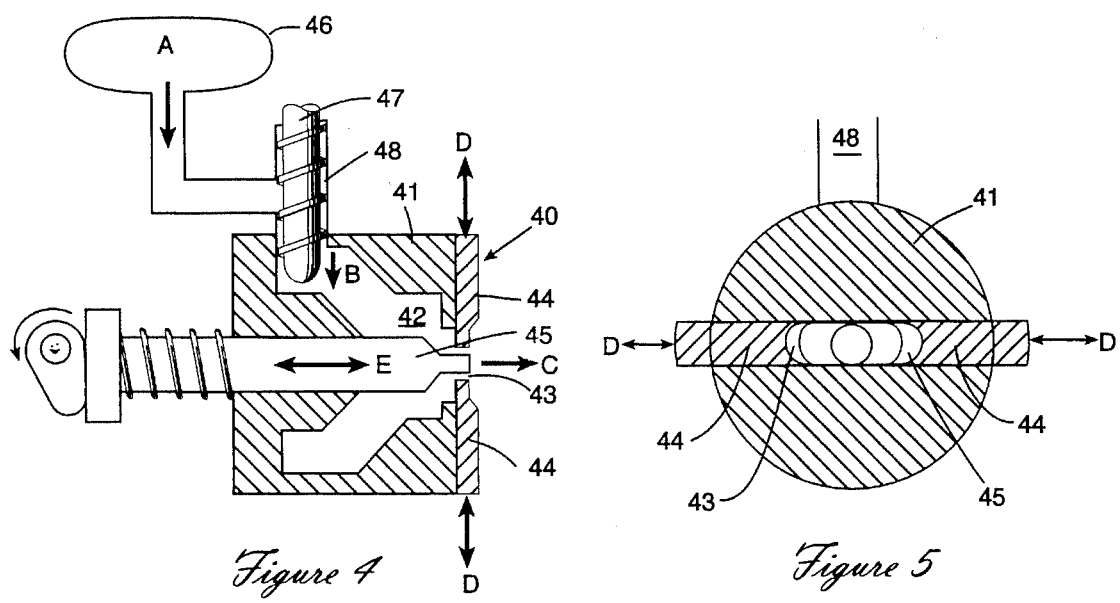
*Figure 4*       *Figure 5*

5,549,579

UNITARY DRAIN AND METHOD FOR MAKING

CROSS REFERENCE TO RELATED APPLICATIONS

This is a continuation of application Ser. No. 08/219,410; filed Mar. 29, 1994, now abandoned, which is a continuation of Ser. No. 07/979,808 filed Nov. 20, 1992, and now abandoned.

BACKGROUND OF THE INVENTION

1. Field of the Invention

This invention relates to implantable fluid conducting tubing for medical use, and more particularly to unitary drainage tubing having a variable outer dimension along its length which is useful for conducting fluids from and/or to a site within the body of a patient.

2. Prior Art

Drainage tubing is frequently used to drain fluids from a wound site following surgery. It may also be used to deliver fluids to a site within the body. Such drains may simply comprise a tubular member, such as a Penrose drain, which is more or less flaccid and biocompatible. One end of the drain is temporarily implantable within the area of the body to be drained while the other end of the tubing extends from the patient to drain into a reservoir such as a bandage or jar. Problems associated with prior art drainage tubes are collapsing and sealage of the drainage conduit due to a lack of structural integrity in the walls of the drainage tube. Another problem is insufficient fenestrations or openings in the collecting end of the drainage tube (the end of the drainage tube embedded in the site to be drained) to facilitate the removal of body fluids therefrom. Yet another problem with prior art drainage tubes is the occlusion of the drainage path by clotted blood or other cellular debris from the wound site.

To overcome these problems, a variety of drainage tubes have been devised. Such tubes include solid implantable members having a tubular or channeled exterior surface which facilitate the drainage of fluid therethrough. Representative of such drainage tubes is the drain catheter described by Blake in U.S. Pat. No. 4,465,481, the disclosure of which is incorporated herein by reference. Such drainage tubes are normally characterized by a substantially uniform outer diameter along their length. Such a construction limits the size of the site to be drained (or perfused) to a relatively small volume immediately surrounding implanted drainage portion of the drainage tube. Others, such as the Jackson-Pratt wound drain are composite structures fabricated by joining together separate parts.

SUMMARY OF THE INVENTION

The term "unitary construction" as used herein, when applied to an article of manufacture such as a drain tube, means an article of manufacture which is fabricated in a single piece, as opposed to an article of manufacture which is fabricated by the joining together of separate parts. Thus, an article of unitary construction is seamless. Similarly, the term "integral" as used herein, when applied to adjacent portions of an article, means that there is no joint, seam, or material boundary between the subject portions.

An object of this invention is to provide a drainage tube for conducting fluids from a wound site to an external reservoir wherein the drainage tube has a large temporarily implantable collecting portion with a large surface area.

Another object of this invention is to provide a tubing of variable outer dimension which is unitary in construction and at least a portion of which is implantable within the body of a patient.

Still another object of this invention is to provide a drainage tube for temporary implantation within a patient which is easily removed by applying traction to the end of the tube extending from the patient without the danger of the drain assembly pulling apart.

Yet another object of this invention is to provide a drainage tube having a lumen which cannot collapse when subjected to reasonable external pressure.

Still another object of this invention is to provide a medically implantable tube which may be used to conduct exogenous fluids to a site within the body.

These and other objects of the invention will become apparent as we turn now to a brief description of the drawings and a description of the preferred embodiment.

BRIEF DESCRIPTION OF THE DRAWINGS

FIG. 1 is perspective view of a drainage tube made in accordance with the present invention.

FIG. 2 is a cross-sectional view of the drainage tube of FIG. 1 taken along section line 2—2.

FIG. 3 is a cross-sectional view of the drainage tube of FIG. 1 taken along section line 3—3.

FIG. 3B is cross-sectional view of the extension tube of FIG. 1 along section line 3B—3B.

FIG. 4 is cross-sectional view of an extruder head showing the relative positions of the mandrel and the die nozzle opening.

FIG. 5 is a front view of the extruder head showing the position of the slides on the die nozzle opening.

BRIEF DESCRIPTION OF THE PREFERRED EMBODIMENT

Figure 6:
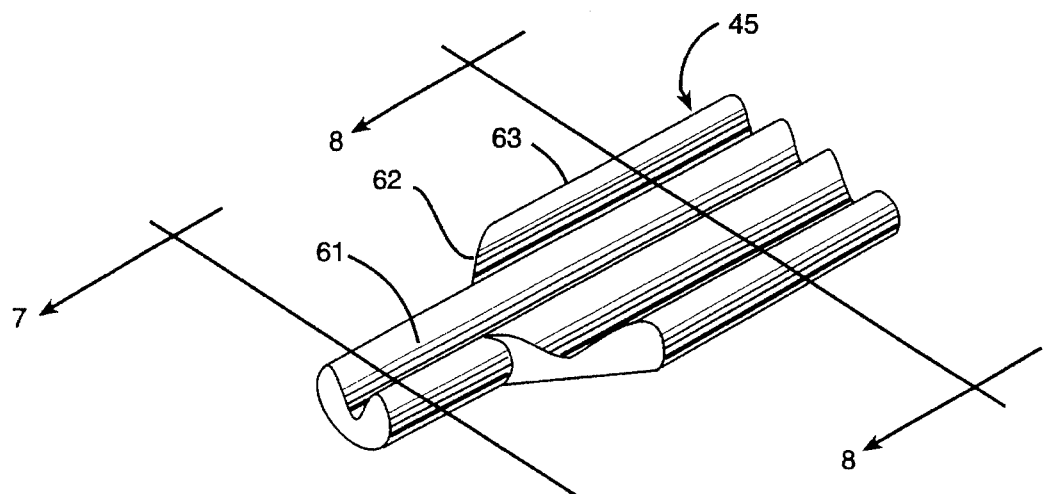
FIG. 6 is a perspective view of the mandrel.
Figure 7:
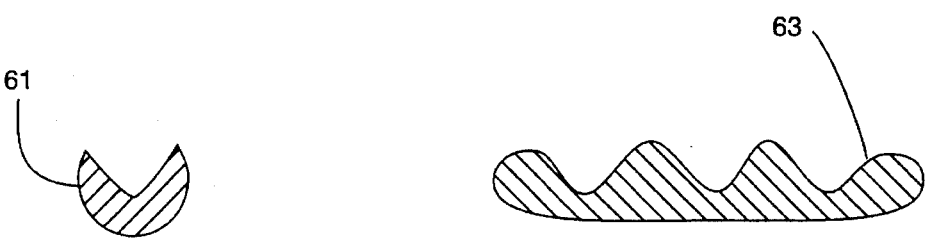
FIG. 7 is a cross-sectional view of the mandrel of FIG. 6 along line 7—7.
Figure 8:
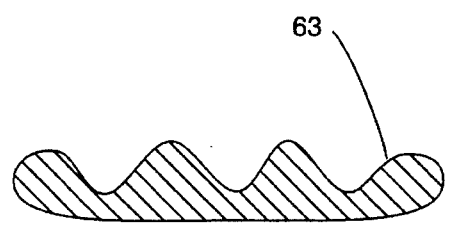
FIG. 8 is a cross-sectional view of the mandrel of FIG. 6 along line 8—8.
Figure 9:
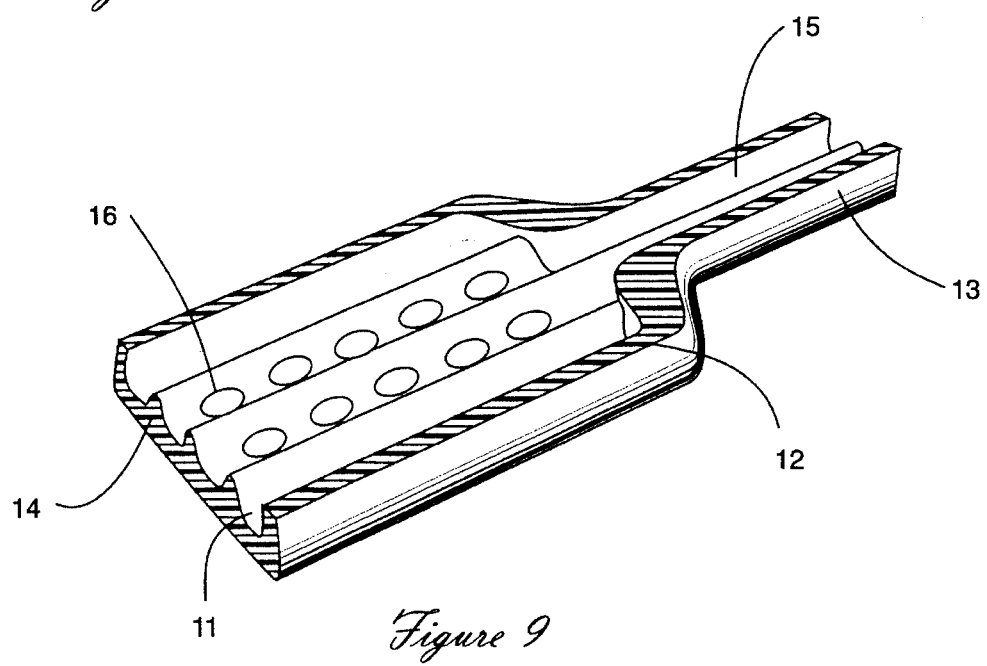
FIG. 9 is a cutaway, longitudinal perspective view of the drainage tubing of the present invention.

FIG. 1 is a perspective view of a drainage tube embodiment of the present invention generally indicated at the numeral 10. The implantable portion of the drainage tube consists of three distinct portions, each portion having a different outer dimension than the other portions: a collecting portion 11, a transition portion 12 and an extension portion 13. The collection portion 11 is preferably a hollow flattened tubular member. Fenestrations 16 may be cut in the wall thereof and distributed in such a manner as to permit the influx of fluids derived from tissues surrounding the collection portion into the central lumen 15 of the collection portion. Preferably a plurality of ribbed members 14 projects from the inner wall of the collection portion throughout the length of the flattened collection portion to prevent the collection portion from collapsing upon itself.

Other features of the collection portion can be seen by turning now to FIG. 2, in which the central lumen 15 appears as a flattened chamber or reservoir surrounded by the walls of the collecting portion. The walls have ribs or struts 14 projecting therefrom, which prevent the collection portion from collapsing; thereby promoting the drainage of fluids collecting in the collection portion into the extension tube. The outer and inner surfaces of the collection portion 11 taper down to coalesce with the outer and inner surfaces of the extension portion by means of the transition portion. This is seen more clearly by viewing a cross section of the transition portion taken along line 3—3. In this section it is seen that the size of the toothlike ribs or struts 14 and the lumen 15 have decreased and taken on a dimension or cross-section more closely approximating that of the cross-section of the extension 13. This gradual tapering of the external surface of the collection portion of the drainage tube enables the tube to be pulled from a wound site, as for example, by traction on the portion of the extension portion which protrudes from the patient without the tearing of tissue. The transition portion, which is integral with both the extension portion and the collection portion, provides a smooth geometric transition between the broadened collection portion and the cylindrical extension portion. This facilitates removal of the tube.

DESCRIPTION OF THE EXTRUDER HEAD

Extruder heads are well known in the art for making tubing such as commonly used in wound drainage devices and the like. Such tubing is normally extruded from an elastomer that is bioacceptable such as polyurethane or silicone. For extremely short periods of use latex may be acceptable. However, many patients are allergic to latex and silicone appears at present to be a more acceptable elastomer for such devices.

An extruder is a device useful for pressing an uncured elastomer through a nozzle or opening having a particular shape. The extruder has a head which consists of three parts: a elastomer chamber, a die and a mandrel. The die forms the opening through which the extrudable material from the elastomer chamber is forced. A mandrel is an obstruction that is placed in the die opening to restrict the distribution of extruded elastomer. Extrudable material is forced around the mandrel as it passes through the die opening. For example, if the mandrel consists of a cylindrical member that projects into and partially obstructs the die opening, the extruded material must pass around the mandrel to emerge from the die opening and therefore a tubing having a cylindrical lumen is produced.

If the mandrel is positioned in the extruder head in such a way that it may be moved with respect to the die opening during extrusion, then various features of an extruded article may be changed during extrusion depending upon the shape of the mandrel and the position of the mandrel with respect to the die opening. For example, if a cylindrical mandrel is placed within a circular die opening, a article extruded therethrough will consist of a tube having a hollow interior cylindrical lumen. If the mandrel is moved backwards, away from the face of the die, the elastomer in the elastomer chamber is no longer forced around the mandrel to exit the die opening but, in fact, forms a solid plug that moves through the die opening. Therefore, if the mandrel, which may vary in shape along its length, is oscillated back and forth with respect to the die opening, and the elastomer continuously forced or pressed through the die opening, the resultant extruded material will comprise a continuous hollow tubing alternating with solid plugs of extrudable material.

The embodiment of the drainage tube of the present invention shown in FIGS. 1 through 3, is conveniently made by an extruder head having features generally indicated in FIG. 4. An extruder head 40 has a die opening 43 and slide means 44 for adjusting the size of the die opening. The extruder head has walls 41 surrounding a chamber 42. An extrudable material (not shown) may be housed in reservoir 46. A screw or other driving means 47 forces the elastomer from the reservoir 46 in the direction of arrows A and B into chamber 42. The extrudable material is preferably an elastomer such as polyurethane or silicone or copolymers thereof. The extrudable material, filling the chamber 42 under pressure, seeks to exit the chamber through the die opening 43. In order to do so, it must pass around the tip of the mandrel 45 centered in the die opening 43. The outer diameter of the extruded material will depend upon the size of the die opening 43, which, in turn, depends upon the position of the die opening slides 44. When the die opening slides 44, which may be moved generally in the direction of ↕D, are fully withdrawn from each other, the die opening 43 becomes a broad horizontal slot and the extruded material passing therethrough will take on the widest outer dimension of the die opening. When the slides are moved together, the outer dimension of the extruded material conforms to the size and shape of the reduced die opening. The mandrel 45 may take on a particular shape or it may take on a plurality of shapes along its length. It may even vary continuously in shape along its length.

Turning now to FIG. 5 we see the front view of an extruder head with the die opening slides 44 in the open position so as to form a horizontal slot with rounded corners. The tip of the mandrel, which is seen at 45, fills a portion of the die opening 43 forcing the extruded material (which is not shown) around the mandrel 45. If the mandrel 45 is fully retracted, that is, drawn back away from the viewer (the plane of the paper) so that it does not project into the die opening, the extruded material will fill the die opening 43 and a solid plug will emerge. If the end of the mandrel 45 is a rounded cylinder and is advanced until the cylinder fills the die opening, then the extruder head would extrude a flattened, more or less rectangular tubing with a circular inner lumen.

A mandrel suitable for making the drainage tube in accordance with the present invention is generally shown in FIG. 6. The mandrel consists of three portions: a mandrel extension, transition and extension portions, which portions correspond reciprocally or matingly to the similar portions on the inner surface of the extruded drainage tube. The mandrel extension portion 61 is a generally cylindrical element which, when interposed within the die opening 43 (FIG. 5), provides a central lumen to the extruded member, the cross-section of the central lumen corresponding substantially to the cross-section of the mandrel extension portion 61. Simultaneously, as the die opening slides 44 are being withdrawn to broaden the die opening, the mandrel 45 is advanced further into the die opening causing the inner lumen of the extruded article to conform to the shape of the mandrel transition portion 62 and the mandrel collection portion 63 respectively. The mandrel transition portion 62 is machined to form a gradual, smooth transition between the outer surface of the mandrel extension portion 61 and the mandrel collection portion 63. Such a mandrel may be machined (for example, from stainless steel) in sections and assembled or machined in a single piece. Such a mandrel may also be cast or molded in a single piece.

It is important that the lateral motion of the die opening slides 44 be synchronized to correspond to the position of the mandrel within the die opening. For example, when the die opening slides 44 are fully open, the drainage tube collector portion is being extruded. The position of the mandrel 45 must be simultaneously advanced (moved to the right in FIG. 4) so that the mandrel collector portion 63 fills the die opening 43 and the inner lumen 15 of the collector portion 11 corresponds to the outer dimension of the mandrel collector portion 63. To facilitate such synchronous positioning of the mandrel 45 within the die opening, with the position of the die opening slides 44, a pair of synchronous motors may conveniently be employed so that the die opening slides make one complete open and close cycle as the mandrel makes one complete forward and reverse cycle. The extruded article comprises a continuous series of drainage tubes which may be cut apart into individual tubes.

What we claim is:

1. In a drainage tube having a proximal end and a distal end including an implantable portion adapted for implantation beneath the skin of a patient, said implantable portion having a length and comprising, in combination:

(a) a hollow tubular collecting portion having a first length, a first outer surface and a first inner surface having struts projecting inward therefrom coextensive with said first length, said first outer surface presenting a uniform first cross-sectional profile along said first length and wherein said first cross-sectional profile has a greatest dimension; and (b) a hollow tubular extension portion having a second length and a second outer surface having a substantially uniform second cross-sectional profile coextensive with said second length, said second cross-sectional profile having a greatest dimension which is less than said greatest dimension of said first cross-sectional profile; and (c) a hollow transition portion therebetween, said transition portion providing an integral connection between the proximal end of said collecting portion and the distal end of said extension portion, said transition portion providing a gradual transition between said first cross-sectional profile and said second cross-sectional profile;

the improvement wherein the greatest dimension of said first cross-sectional profile and the greatest dimension of said second cross-sectional profile of said implantable portion of said drainage tube progressively decreases along said length of said implantable portion in the direction of said proximal end of said drain, and wherein said implantable portion is of unitary construction.

\* \* \* \* \*